United States Patent [19]
Arrowsmith et al.

[11] Patent Number: 5,158,964
[45] Date of Patent: Oct. 27, 1992

[54] BENZOXAZOLE SULFONAMIDE ANTI-ARRHYTHMIC AGENTS

[75] Inventors: John E. Arrowsmith, Deal; Peter E. Cross, Canterbury; Geoffrey N. Thomas, Sandwich, all of England

[73] Assignee: Pfizer Inc., New York, N.Y.

[21] Appl. No.: 727,040

[22] Filed: Jul. 8, 1991

Related U.S. Application Data

[62] Division of Ser. No. 529,984, May 29, 1990, Pat. No. 5,055,473, which is a division of Ser. No. 151,390, Feb. 2, 1988, Pat. No. 4,956,382.

[30] Foreign Application Priority Data

Feb. 7, 1987 [GB] United Kingdom ............... 87-02789

[51] Int. Cl.$^5$ ............................................. A61K 31/42
[52] U.S. Cl. ..................................... 514/367; 514/375; 514/394; 548/178; 548/179; 548/217; 548/309.7
[58] Field of Search ............... 548/152, 179, 217, 178; 514/367, 375

[56] References Cited

U.S. PATENT DOCUMENTS 4,581,457  4/1986  Musser et al. ........................ 548/179
4,956,382  9/1990  Arrowsmith et al. ............... 514/443
4,990,509  2/1991  Arrowsmith et al. ............... 544/237
5,055,473  10/1991  Arrowsmith et al. ............. 544/311
5,070,096  12/1991  Mohrs et al. ........................ 546/153

*Primary Examiner*—Donald G. Daus
*Attorney, Agent, or Firm*—Peter C. Richardson; Paul H. Ginsburg

[57] ABSTRACT

A series of novel N-alkyl N-(alkanesulphonamidoheterocyclicmethyl)-4-alkanesulphonamidophenethylamines have been prepared, including their pharmaceutically acceptable salts and various key novel intermediates therefor. The heterocyclic moiety present in these compounds is a benzo-fused heterocyclic group derived from either benzofuran, benzothiophene, benzoxazole or quinoline, and it is attached to the adjacent methyl group of the molecule by means of the available ring carbon atom which is situated alpha to the hetero atom. These particular compounds are useful in therapy as highly effective anti-arrhythmic agents and therefore, are of value in the treatment of various cardiac arrhythmias. Preferred member compounds include N-methyl-N-(5 methanesulphonamidobenzofur-2-ylmethyl)-4-methanesulphonamidophenethylamine and N-methyl-N-(6 methanesulphonamidoquinol-2-ylmethyl)-4-methanesulphonamidophenethylamine. Methods for preparing all these compounds from known starting materials are provided.

8 Claims, No Drawings

BENZOXAZOLE SULFONAMIDE ANTI-ARRHYTHMIC AGENTS

This is a division of application Ser. No. 07/529,984, filed on May 29, 1990 and now U.S. Pat. No. 5,055,473, which is, in turn, a division of application Ser. No. 07/151,390, filed on Feb. 2, 1988 and now U.S. Pat. No. 4,956,382.

BACKGROUND OF THE INVENTION

This invention relates to certain sulfonamides which are antiarrhythmic agents, and to intermediates therefor.

The compounds of the invention prolong the duration of the action potential in cardiac muscle and conducting tissue, and thereby increase refractoriness to premature stimuli. Thus, they are Class III antiarrhythmic agents according to the classification of Vaughan Williams (Anti-Arrhythmic Action, E. M. Vaughan Williams, Academic Press, 1980). They are effective in atria, ventricles and conducting tissue both in vitro and in vivo and are therefore useful for the prevention and treatment of a wide variety of ventricular and supraventricular arrhythmias including atrial and ventricular fibrillation. Because they do not alter the speed at which impulses are conducted, they have less propensity than current drugs (mostly Class I) to precipitate or aggravate arrhythmias, and also produce less neurological side effects. Some of the compounds also have some positive inotropic activity and therefore are particularly beneficial in patients with impaired cardiac pump function.

SUMMARY OF THE INVENTION

Thus the invention provides compounds of the formula:

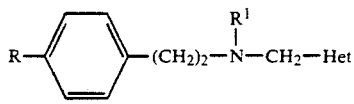
(A)

and their salts, where
R is $-NO_2$, $-NH_2$ or $-NHSO_2(C_1-C_4$ alkyl);
$R^1$ is $C_1-C_4$ alkyl;
and "Het" is a group of the formula:

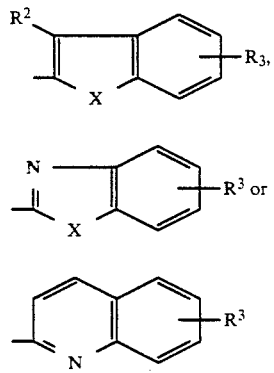

where $R^2$ is H, $CH_3$ or $C_2H_5$; $R^3$ is $-NO_2$, $-NH_2$ or $-NHSO_2 (C_1-C_4$ alkyl); and X is O, S or $NR^4$ where $R^4$ is H or $CH_3$; with the proviso that when one of R and $R^3$ is $-NO_2$, then the other is not $-NH_2$.

The compounds of the formula (A) in which R and $R^3$ are $-NHSO_2(C_1-C_4$ alkyl) have activity as antiarrhythmic agents. The remaining compounds are synthetic intermediates.

Thus the invention also provides antiarrhythmic agents of the formula:

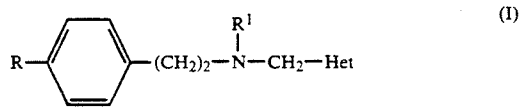
(I)

and their pharmaceutically acceptable salts, where
R is $-NHSO_2(C_1-C_4$ alkyl);
$R^1$ is $C_1-C_4$ alkyl; and
"Het" is a group of the formula:

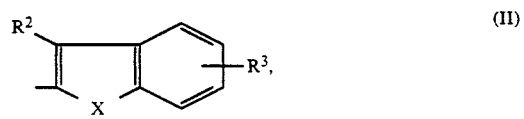
(II)

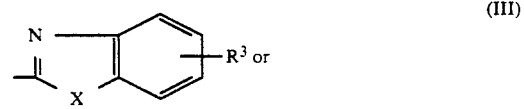
(III)

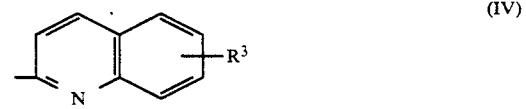
(IV)

where $R^2$ is H, $CH_3$ or $C_2H_5$; $R^3$ is $-NHSO_2(C_1-C_4$ alkyl); and X is O, S or $NR^4$ where $R^4$ is H or $CH_3$.

In the compounds (I), R is preferably $-NHSO_2CH_3$, $R^1$ is preferably $CH_3$ or $C_2H_5$, $R^2$ is preferably H or $CH_3$, $R^3$ is preferably $-NHSO_2CH_3$, and X is preferably O or S.

The substituent $R^3$ is preferably in the 6- or 7- position when "Het" contains a quinolyl group, and in the 5- or 6-position otherwise (i.e., when the benzene ring is fused to a 5-membered heterocycle).

Accordingly, one group of compounds of especial interest in the present invention is that of structural formula (I) wherein "Het" is 5-methanesulphonamidobenzofur-2-yl-, 6-methanesulphonamidobenzofur-2-yl, 3-methyl-5-methanesulphonamidobenzofur-2-yl, 5-methanesulphonamidobenzoxazol-2-yl or 6-methanesulphonamidoquinol-2-yl. Another group of compounds of especial interest is that of the same aforesaid structural formula wherein R is $-NHSO_2CH_3$, $R^1$ is methyl or ethyl, and "Het" is as previously defined elsewhere in the specification by structural formulae (II), (III) and (IV) wherein $R^2$ is hydrogen or methyl, $R^3$ is $-NHSO_2CH_3$ and X is oxygen or sulfur. Preferred compounds within the latter group include those wherein $R^1$ is methyl, $R^2$ is hydrogen and X is oxygen.

More particularly, a most preferred group of compounds of the present invention is that of structural formula (I) wherein R is $-NHSO_2CH_3$, $R^1$ is methyl or ethyl, and "Het" is benzo-fused heterocyclic group of the formula:

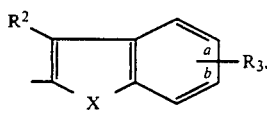

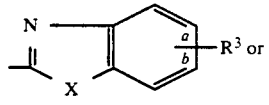

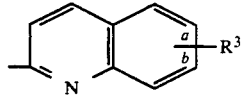

wherein R² is hydrogen or methyl, X is oxygen or sulfur and R³ is —NHSO₂CH₃, with said R³ being attached to either the a- or b-position of "Het".

The preferred individual compounds have the formulae:

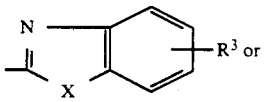

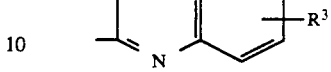

wherein R² is hydrogen, methyl or ethyl; R³ is nitro or amino; and X is oxygen, sulfur, imino or N-methyliminio; with the proviso that when one of R and R³ is nitro, then the other is not amino. These particular compounds are useful as intermediates for the production of the final medicinal products of formula (I), which are of value as anti-arrhythmic agents, as determined by the test procedure that will hereinafter be described in some detail.

For assessment of effects of the compounds on atrial

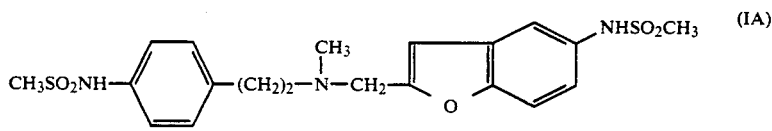

and

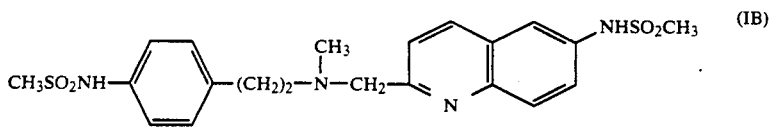

The pharmaceutically acceptable salts of the compounds of the formula (I) include acid addition salts formed from acids which form non-toxic acid addition salts containing pharmaceutically acceptable anions, such as hydrochloride, hydrobromide, hydroiodide, sulphate or bisulphate, phosphate or hydrogen phosphate, acetate, maleate, fumarate, lactate, tartrate, citrate, gluconate, benzoate, methanesulphonate, besylate and p-toluenesulphonate salts. The salts are preparable by conventional techniques.

As previously indicated, there is also included within the purview of this invention various novel intermediate compounds of the formula:

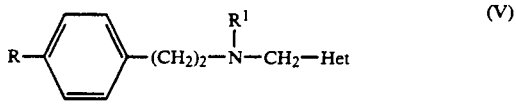

wherein
R is nitro or amino;
R¹ is C₁-C₄ alkyl; and
"Het" is a benzo-fused heterocyclic group of the formula:

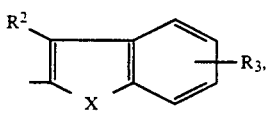

refractoriness, guinea pig right hemiatria are mounted in a bath containing physiological salt solution, and one end is connected to a force transducer. Tissues are stimulated at 1 Hz using field electrodes. Effective refractory period (ERP) is measured by introducing premature stimuli (S₂) after every 8th basic stimulus (S₁). The S₁S₂ coupling interval is gradually increased until S₂ reproducibly elicits a propagated response. This is defined as the ERP. The concentration of compound required to increase ERP by 25% (ED₂₅) is then determined. ERP is also measured in guinea pig right papillary muscles incubated in physiological salt solution. Muscles are stimulated at one end using bipolar electrodes and the propagated electrogram is recorded at the opposite end via a unipolar surface electrode. ERP is determined as above using the extrastimulus technique. Conduction time is obtained from a digital storage oscilloscope by measuring the interval between the stimulus artefact and the peak of the electrogram (i.e. the time required for the impulse to travel along the length of the muscle).

Atrial and ventricular ERP's are also measured in anaesthetised or conscious dogs by the extrastimulus technique whilst the atrium or right ventricle is being paced at a constant rate.

The compounds of the formula (I) can be administered alone but will generally be administered in admixture with a pharmaceutical carrier selected with regard to the intended route of administration and standard pharmaceutical practice. They can be administered both to patients suffering from arrhythmias and also prophylactically to those likely to develop arrhythmias.

For example they may be administered orally in the form of tablets containing such excipients as starch of lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic.

For administration to man in the curative or prophylactic treatment of cardiac conditions such as ventricular and supraventricular arrhythmias, including atrial and ventricular fibrillation, it is expected that oral dosages of the compounds of the formula (I) will be in the range from 2 to 150 mg daily, taken in and up to 4 divided doses per day, for an average adult patient (70 kg). Dosages for intravenous administration would be expected to be within the range 1.0 to 20 mg per single dose as required. A severe cardiac arrythmia is preferably treated by the i.v. route in order to effect a rapid conversion to the normal rhythm. Thus for a typical adult patient individual tablets or capsules might contain 2 to 50 mg of active compound, in a suitable pharmaceutically acceptable vehicle or carrier. Variations may occur depending on the weight and condition of the subject being treated as will be known to medical practitioners.

Thus the present invention provides a pharmaceutical composition comprising a compound of the formula (I) as defined above or pharmaceutically acceptable salt thereof, together with a pharmaceutically acceptable diluent or carrier.

The invention also provides a method of preventing or reducing cardiac arrhythmias in a human being, which comprises administering to said human an effective amount of a compound of the formula (I) or pharmaceutically acceptable salt thereof, or of a pharmaceutical composition as defined above.

The invention yet further provides a compound of the formula (I) or a pharmaceutically acceptable salt thereof, for use as a medicament, particularly for use as an antiarrhythmic agent.

The invention also provides the use of a compound of the formula (I), or of a pharmaceutically acceptable salt thereof, for the manufacture of a medicament for the prevention or reduction of cardiac arrhythmias.

DETAILED DESCRIPTION OF THE INVENTION

The compounds of the formula (I) can be prepared by the following general routes:

(1) The first route involves the acylation of a compound of the formula (A) in which R and/or $R^3$ is —$NH_2$, using a $C_1$-$C_4$ alkanesulphonyl chloride or bromide, or a $C_1$-$C_4$ alkanesulphonic anhydride. When both R and $R^3$ are —$NH_2$, clearly at least two equivalents of the acylating agent will be required and, of course, R and $R^3$ in the final product will be the same.

The reaction is typically carried out at room temperature, and optionally in the presence of an acid acceptor such as pyridine, triethylamine, potassium carbonate or sodium bicarbonate. The presence of an acid acceptor is particularly useful when an alkanesulphonyl chloride or bromide is used. It is in fact particularly convenient to carry out the reaction with an alkanesulphonyl chloride in pyridine. The product of the formula (I) can then be isolated and purified by conventional means.

The starting materials for this acylation reaction are available conventionally, e.g. as follows:

(a)

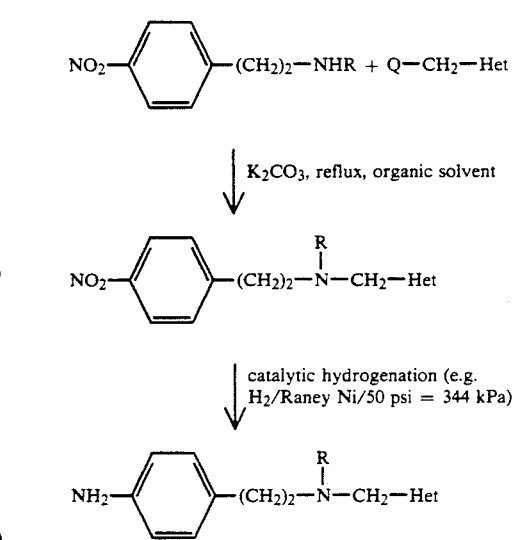

R and "Het" are as defined for formula (I), and Q is a leaving group such as chloro, bromo, iodo or methanesulphonyloxy.

(b)

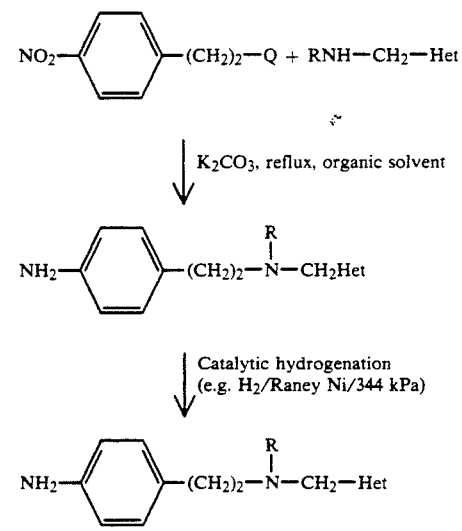

R, Het and Q are as defined in (a) above.

(c) Routes (a) and (b) can also be carried out using starting materials in which the substituent $R^3$ on "Het" is nitro instead of $C_1$-$C_4$ alkanesulphonamido, thus producing a di-nitro intermediate which can be reduced by catalytic hydrogenation to a di-amino starting material, i.e., a starting material of the formula (A) in which both R and $R^3$ are amino.

and (d)

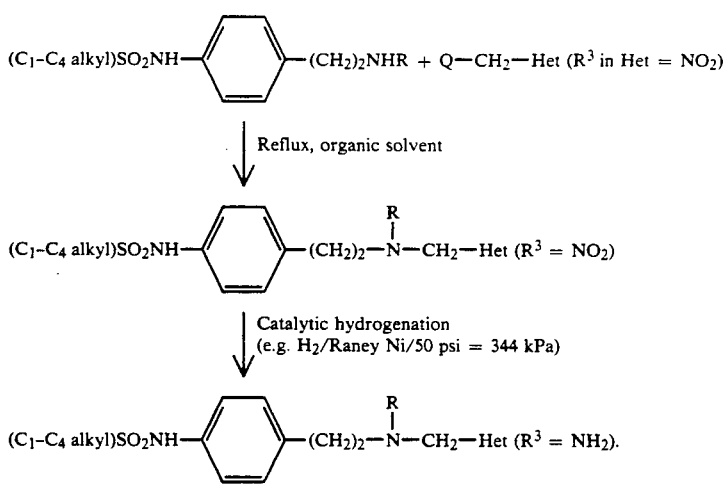

R is $C_1$-$C_4$ alkyl, "Het" in the first step is a nitro-substituted heterocycle as defined for formula (A), and Q is a leaving group as defined in (a) above.

The starting materials used in methods (a) to (d) are either known compounds or can be prepared by conventional techniques, e.g. by the techniques illustrated in the following Preparations.

(2) The second route to the compounds (I) can be illustrated as follows:

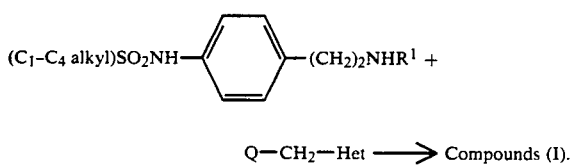

Q—$CH_2$—Het ⟶ Compounds (I).

or ($C_1$-$C_4$ alkyl)$SO_2$NH—⟨⟩—$(CH_2)_2$—Q +

RNH—$CH_2$—Het ⟶ Compounds (I).

$R^1$ is $C_1$-$C_4$ alkyl, "Het" is as defined for formula (I), and Q is a leaving group such as chloro, bromo, iodo, $C_1$-$C_4$ alkanesulphonyloxy (preferably methanesulphonyloxy), benzenesulphonyloxy or toluenesulphonyloxy. The reaction is typically carried out in an organic solvent at up to the reflux temperature. It is preferred to carry out the reaction under reflux. The presence of an acid acceptor is optional but is most useful when Q is Cl, Br or I. Typical acid acceptors are pyridine, triethylamine, potassium carbonate and sodium bicarbonate. The starting materials are again known compounds or can be obtained conventionally.

The following Examples, in which all temperatures are in °C., illustrate the preparation of the compounds of the formula (I):

EXAMPLE 1

N-Methyl-N-(3-methyl-5-methanesulphonamidobenzofur-2-ylmethyl)-4-methanesulphonamidophenethylamine

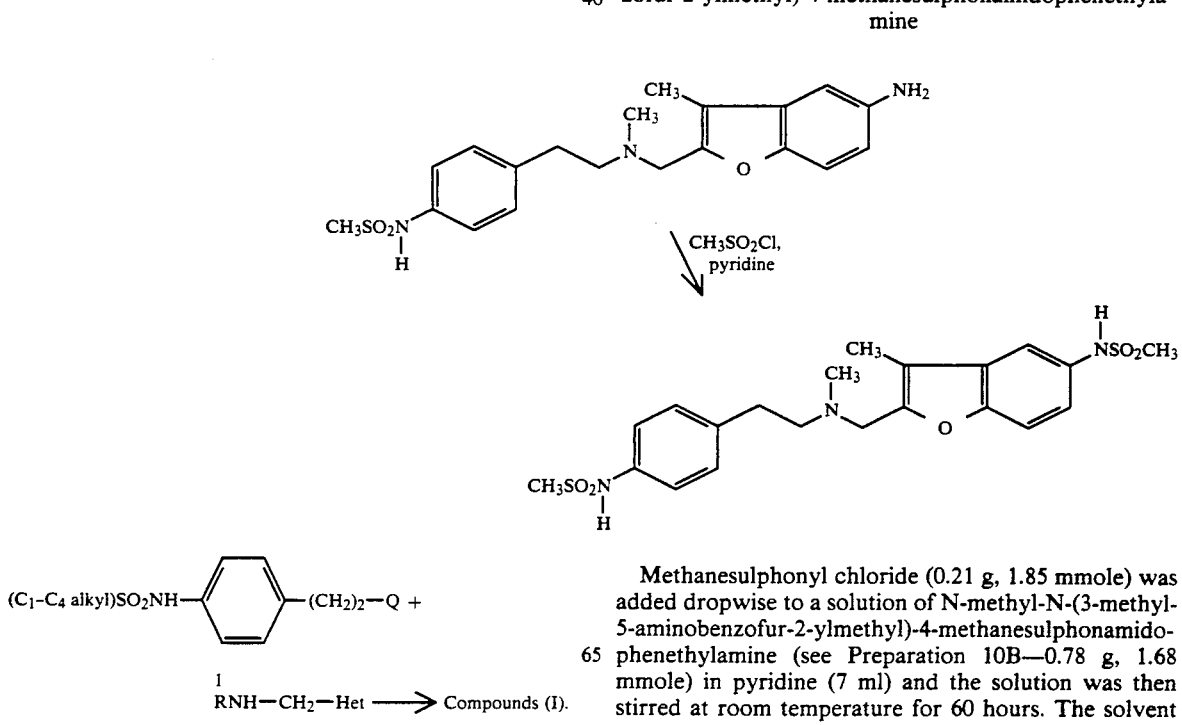

Methanesulphonyl chloride (0.21 g, 1.85 mmole) was added dropwise to a solution of N-methyl-N-(3-methyl-5-aminobenzofur-2-ylmethyl)-4-methanesulphonamidophenethylamine (see Preparation 10B—0.78 g, 1.68 mmole) in pyridine (7 ml) and the solution was then stirred at room temperature for 60 hours. The solvent was evaporated and the residue triturated with toluene.

The toluene was decanted, the residue stirred with aqueous sodium bicarbonate, and the precipitate collected by filtration and recrystallised from methanol to give the title compound, yield 0.38 g, m.p. 142°–143.5°.

Analysis %: Found: C,54.4; H,5.8; N,9.1; Calculated for $C_{21}H_{27}N_3O_5S_2$: C,54.2; H,5.85; N,9.0.

EXAMPLE 2

N-Methyl-N-(5-methanesulphonamidobenzofur-2-ylmethyl)-4-methanesulphonamidophenethylamine

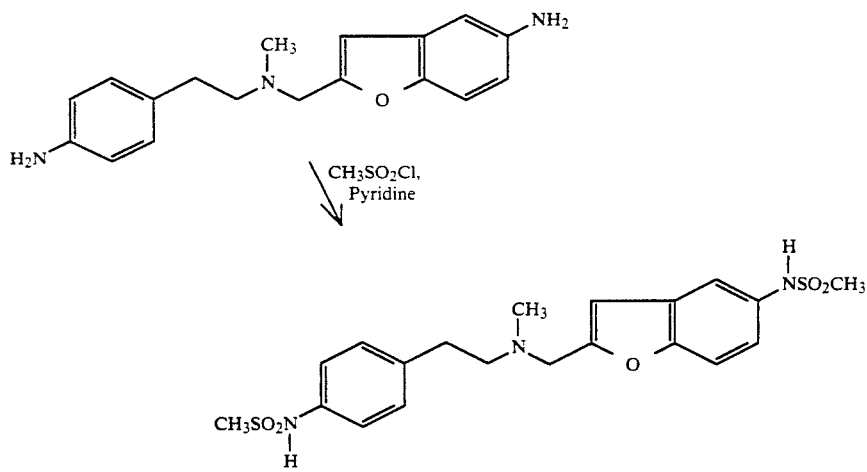

Methanesulphonyl chloride (0.76 g, 6.6 mmole) was added dropwise to a solution of N-methyl-N-(5-aminobenzofur-2-ylmethyl)-4-aminophenethylamine (see Preparation 3—0.9 g, 3.0 mmole) in pyridine (25 ml) and the mixture was stirred at room temperature for 18 hours. The solvent was then evaporated and the residue diluted with aqueous sodium bicarbonate and extracted three times with methylene chloride. The combined organic extracts were dried (MgSO$_4$) and evaporated, and the residue was purified by chromatography on silica eluting with ethyl acetate. The product-containing fractions were combined, evaporated and the resulting solid was recrystallised from ethyl acetate/methanol to give the title compound, yield 0.35 g, m.p. 177°–179°.

Analysis %: Found: C,53.2; H,5.7; N,9.0; Calculated for $C_{20}H_{25}N_3O_5S_2$: C,53.2; H,5.6; N,9.3.

EXAMPLE 3

N-Methyl-N-(5-methanesulphonamidobenzoxazol-2-ylmethyl)-4-methanesulphonamidophenethylamine

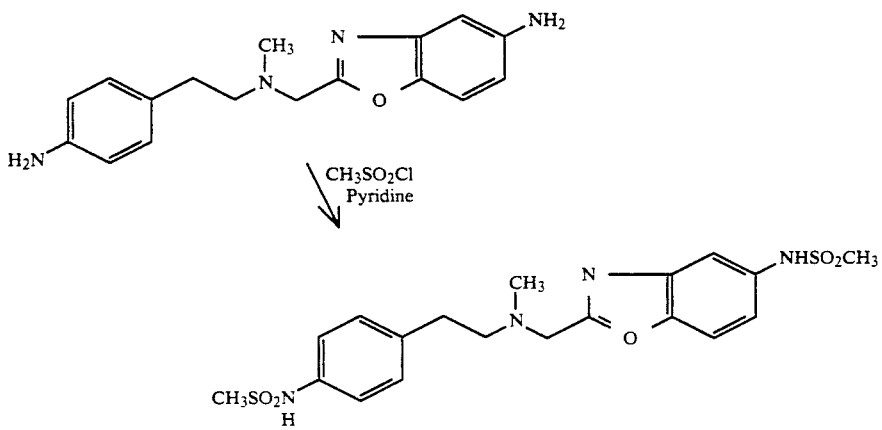

Methanesulphonyl chloride (0.38 g, 3.3 mmole) and N-methyl-N-(5-aminobenzoxazol-2-ylmethyl)-4-aminophenethylamine (see Preparation 1C—0.45 g, 1.5 mmole) in pyridine (20 ml) when reacted together under conditions similar to those of Example 2 gave the title compound, yield from ethanol 0.25 g, m.p. 174°–176°.

Analysis %: Found: C,50.4; H,5.1; N,12.4; Calculated for $C_{19}H_{24}N_4O_5S_2$: C,50.4; H,5.35; N,12.4.

EXAMPLE 4

N-Methyl-N-(6-methanesulphonamidobenzofur-2-ylmethyl)-4-methanesulphonamidophenethylamine

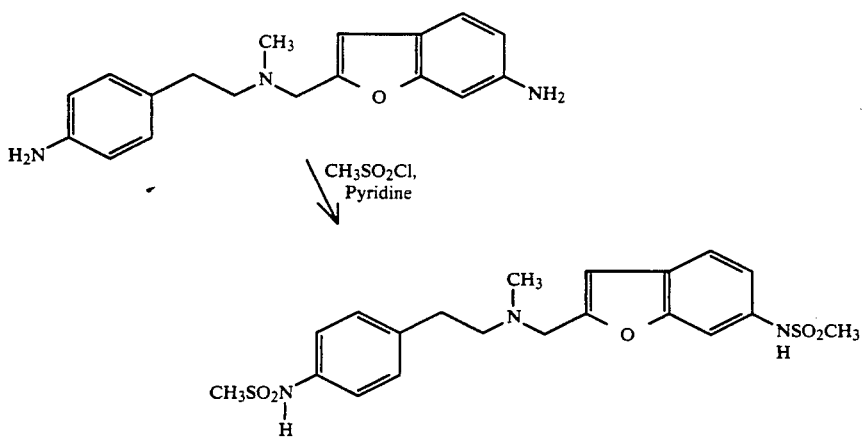

Methanesulphonyl chloride (0.21 g, 1.8 mmole) and N-methyl-N-(6-aminobenzofur-2-ylmethyl)-4-aminophenethylamine (see Preparation 2—0.24 g, 0.82 mmole) in pyridine (3 ml) when reacted together under conditions similar to those of Example 2, gave the title compound as an oil, yield 0.18 g.

Analysis %: Found: C,53.0; H,5.7; N,9.1; Calculated for $C_{20}H_{25}N_3O_5S_2$: C,53.2; H,5.6; N,9.3.

EXAMPLE 5

N-Methyl-N-(6-methanesulphonamidoquinol-2-ylmethyl)-4-methanesulphamidophenethylamine Methanesulphonyl chloride (0.15 g, 1.3 mmole) and N-methyl-N-(6-aminoquinol-2-ylmethyl)-4-aminophenethylamine (see Preparation 4—0.17 g, 0.37 mmole) in pyridine (20 ml) when reacted together under conditions similar to those of Example 2 gave the title compound, yield 0.70 g from ethyl acetate, m.p. 163°–165°.

Analysis %: Found: C,54.3; H,5.45; N,12.1; Calculated for $C_{21}H_{26}N_4O_4S$: C,54.5; H,5.7; N,12.1.

EXAMPLE 6

N-Methyl-N-[5-methanesulphonamido-2-benzo[b]-thienylmethyl]-4-methanesulphonamidophenethylamine

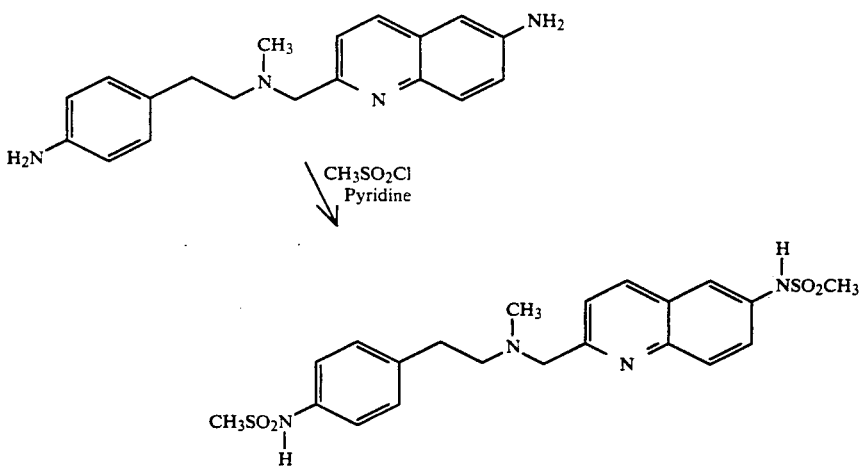

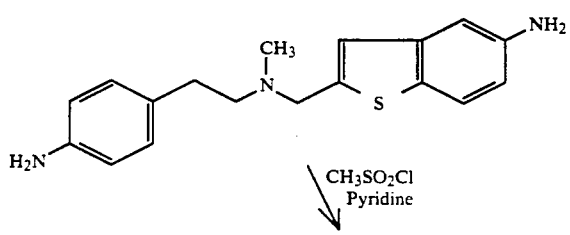

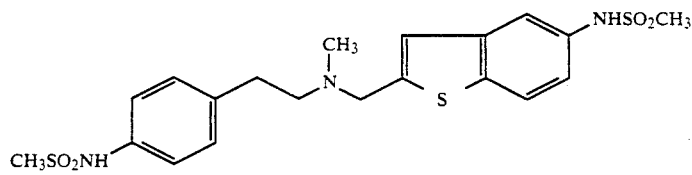

Treatment of N-methyl-N-(5-amino-2-benzo[b]-thienylmethyl)-4-aminophenethylamine (0.26 g—see Preparation 13) with methanesulphonyl chloride (0.23 g) in pyridine according to the method of Example 2 gave the title compound, (0.167 g), m.p. 175°–177°.

Analysis %: Found: C,50.99; H,5.39; N,8.93; Calculated for $C_{20}H_{25}N_3O_4S_3$: C,51.37; H,5.39; N,8.99.

EXAMPLE 7

N-Ethyl-N-(6-methanesulphonamidoquinol-2-ylmethyl)-4-methanesulphonamidophenethylamine hydrochloride

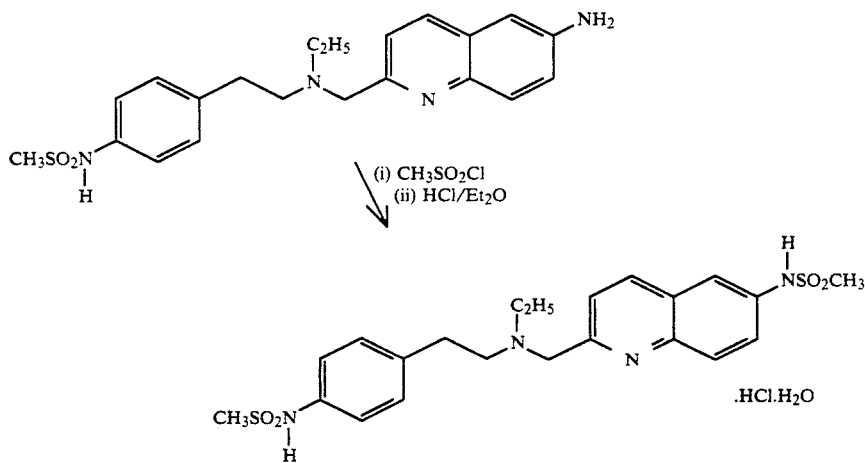

Methanesulphonyl chloride (0.1 g, 1.29 mmole) was reacted with N-ethyl-N-(6-aminoquinol-2-ylmethyl)-4-methanesulphonamidophenethylamine (see Preparation 11B—0.51 g, 1.23 mmole) in pyridine similarly to the procedure of Example 2, giving the free base of the title compound as a gum. The gum was dissolved in ethyl acetate and the solution was diluted with ethereal hydrogen chloride and evaporated to dryness. The residue was triturated with ether to give the title compound as a foam, yield 0.06 g, m.p. 96°.

Analysis %: Found: C,50.2; H,5.5; N,10.0; Calculated for $C_{22}H_{28}N_4O_4S_2.HCl.H_2O$: C,49.75; H,5.9; N,10.5.

EXAMPLE 8

N-(6-Methanesulphonamido-2-quinolylmethyl)-N-methyl-4-methanesulphonamidophenethylamine

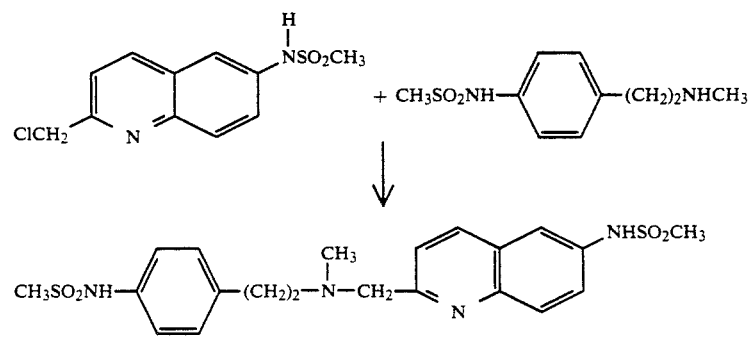

4-[2-(Methylamino)ethyl]methanesulphonanilide (0.228 g, 1 mmol—see Preparation 14(B)) and 2-chloromethyl-6-methanesulphonamidoquinoline (0.135 g, 0.5 mmol—see Preparation 12(D)) were heated in ethanol solution (5 ml) at reflux for 4 hours. The solvent was then evaporated in vacuo and the residue dissolved in methylene chloride, washed with water, dried (MgSO$_4$), filtered and evaporated in vacuo. The resulting gum was purified by column chromatography on silica eluting with methylene chloride containing methanol (0% up to 1%). The product-containing fractions were combined and evaporated in vacuo to give a foam which crystallised from ethanol, yield of the title compound 0.45 g, m.p. 165°–166°, confirmed spectroscopically to be identical to the product of Example 5.

The following Preparations, in which all temperatures are in °C., illustrate the preparation of novel starting materials:

PREPARATION 1

(A) 2-Chloromethyl-5-nitrobenzoxazole

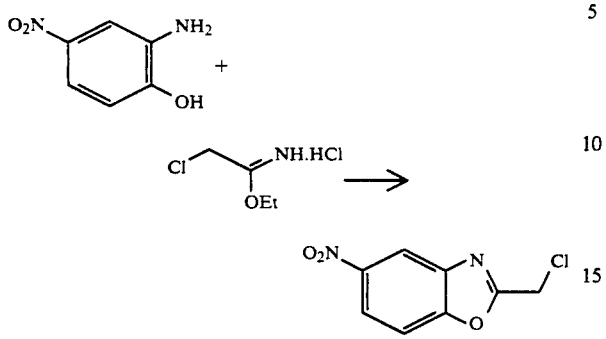

2-Amino-4-nitrophenol (10 g, 65 mmole) and ethyl chloroacetimidate hydrochloride (15.4 g, 97.5 mmole) were heated at reflux temperature in ethanol (100 ml) for 18 hours. The solvent was then removed by evaporation in vacuo and the residue recrystallised from ethanol to give the title compound, yield 9.0 g, m.p. 216°–217°.

Analysis %: Found: C,45.15; H,2.3; N,13.25; Calculated for $C_8H_5ClN_2O_3$: C,45.2; H,2.4; N,13.2.

(B) N-methyl-N-(5-nitrobenzoxazol-2-ylmethyl)-4-nitrophenethylamine

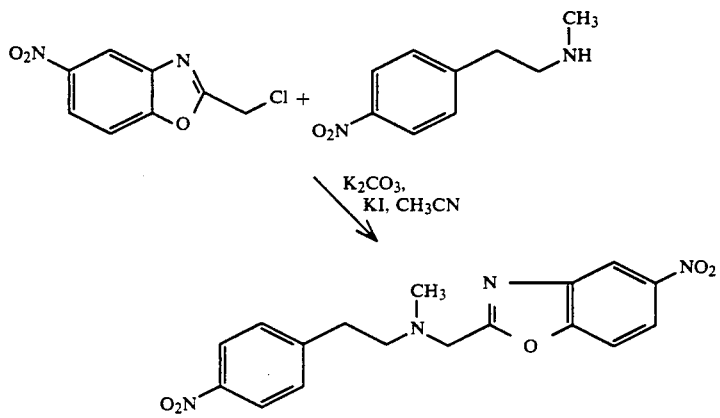

2-Chloromethyl-5-nitrobenzoxazole (2.85 g, 13.4 mmole), N-methyl-4-nitrophenethylamine (J. O. C., [1956], 21, 45) (2.2 g, 12.2 mmole), potassium carbonate (1.85 g, 13.4 mmole) and sodium iodide (2.0 g, 13.4 mmole) were heated under reflux in acetonitrile (50 ml) for 3 days. The solvent was then evaporated, the residue diluted with water, and extracted three times with methylene chloride. The combined organic extracts were washed with water, dried (MgSO$_4$), filtered and evaporated to dryness. The resultant oil was diluted with ether and the supernatant decanted and evaporated to dryness to give an orange solid, which was recrystallised from isopropanol to give the title compound, yield 0.80 g.

$^1$H-N.m.r. (CDCl$_3$): δ=8.6 (d, 1H); 8.3 (dd, 1H); 8.1 (d, 2H); 7.6 (d, 1H); 7.35 (d, 2H); 3.95 (s, 2H); 2.95 (q, 2H); 2.85 (q, 2H); 2.5 (s, 3H) p.p.m.

(C) N-Methyl-N-(5-aminobenzoxazol-2-ylmethyl)-4-aminophenethylamine

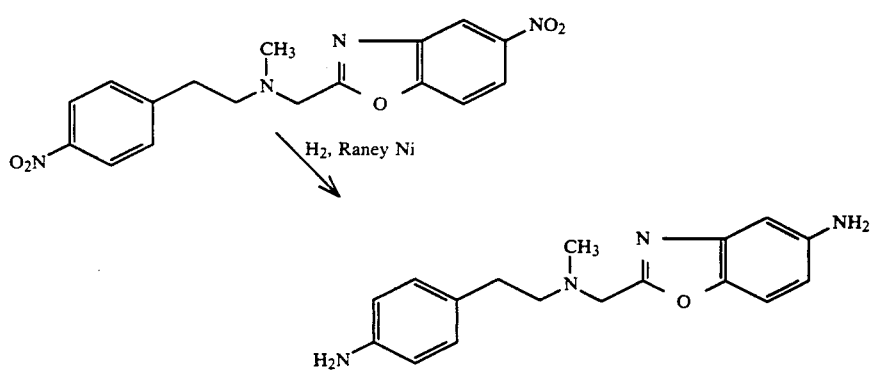

N-Methyl-N-(5-nitrobenzoxazol-2-ylmethyl)-4-nitrophenethylamine (0.78 g, 2.2 mmole) in ethanol (50 ml) containing Raney nickel (0.1 g) was stirred under a hydrogen atmosphere (50 psi=344.7 kPa) for 18 hours, by which time thin layer chromatographic analysis showed that all the starting material had been consumed [silica chromatography plates using methylene chloride/methanol (19:1) as the solvent]. The reaction mixture was then filtered and evaporated to give an oil which was azeotroped with toluene and triturated with ether. The decanted ether was evaporated to give the title compound as an oil, which was used directly without further purification, yield 0.45 g.

$^1$H-N.m.r. (CDCl$_3$): δ=7.25 (d, 1H); 6.95 (dd, 3H); 6.65 (dd, 1H); 6.6 (d, 2H); 3.85 (s, 2H); 2.7 (s, 4H); 2.4 (s, 3H).

PREPARATIONS 2 TO 4

The compounds of Preparations 2 and 3 were prepared similarly to Preparation 1(C) by the reduction of the corresponding di-nitro compounds (see Preparations 6 and 5) using H$_2$/Raney Ni/ethanol/50 p.s.i./room temperature using reaction times of, respectively, 4 and 17 hours. The compound of Preparation 4 was prepared similarly to Preparation 1(C) but using H$_2$/Pd/C in ethanol at 30 p.s.i. for 3 hours, the relevant di-nitro starting material being the subject of Preparation 8.

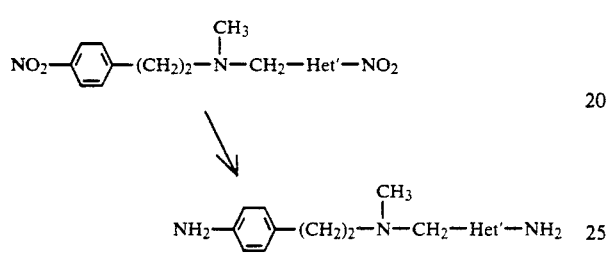

| Preparation No. | -Het'-NO$_2$ | -Het'-NH$_2$ | $^1$H-N.m.r. |
|---|---|---|---|
| 2 | | | δ (CDCl$_3$) = 7.25 (d, 1H); 6.95 (d, 2H); 6.75 (s, 1H); 6.65 (s, 1H); 6.6 (d, 2H); 6.4 (s, 1H); 3.65 (s, 2H); 2.6 (m, 4H); 2.3 (s, 3H). |
| 3 | | | δ (DMSO/TFA) = 7.75 (d, 2H); 7.3 (m, 5H); 4.7 (d, 2H); 3.4 (q, 4H); 2.85 (s, 3H). |
| 4 | | | — |

30 p.s.i. is equivalent to 206.8 kPa, and 50 p.s.i. to 344.7 kPa.

PREPARATION 5

(A) 4-(Isopropylideneaminoxy)nitrobenzene

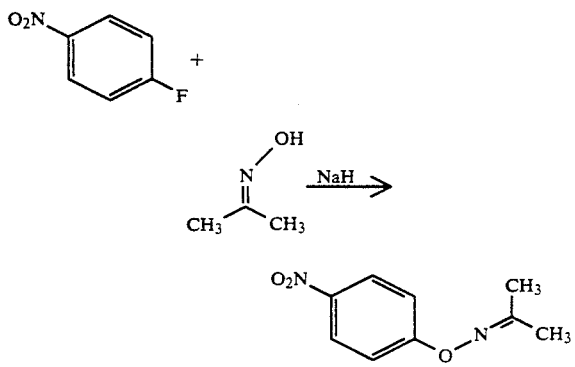

A solution of propanone oxime (30 g, 0.4 mole) in dry tetrahydrofuran (300 ml) was added slowly to a suspension of sodium hydride (10.8 g, 0.45 mole) in dry tetrahydrofuran (50 ml). After gas evolution was complete, dimethylsulphoxide (100 ml) and 4-fluoronitrobenzene (57.85 g, 0.41 mole) were added and the reaction mixture was stirred at room temperature for 2 hours. The reaction mixture was then poured into water and extracted three times with ether. The combined ether extracts were washed with water, dried (MgSO$_4$) and evaporated to give the title compound which was granulated in hexane and filtered, yield 67 g. A sample (7 g) was recrystallised from ethanol, yield 5 g, m.p. 104°–106°.

Analysis %: Found: C,55.6; H,5.05; N,14.35; Calculated for C$_9$H$_{10}$N$_2$O$_3$: C,55.7; H,5.2; N,14.4.

(B) 2-Methyl-5-nitrobenzofuran

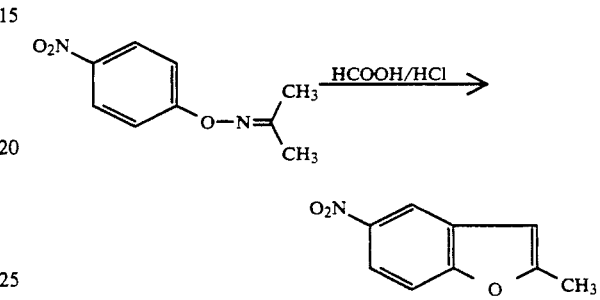

4-(Isopropylideneaminoxy)nitrobenzene (60 g, 0.309 mole) was added to glacial acetic acid (530 ml) containing gaseous hydrogen chloride (25 g) and the mixture was heated at 100° for 18 hours. The solvent was evaporated and the residue azeotroped with cyclohexane to give an oil which was diluted with water and extracted three times with methylene chloride. The combined organic extracts were washed with 10% aqueous sodium hydroxide solution and water, dried (MgSO$_4$) and evaporated to give the title compound, yield 46 g. A sample (5 g) was recrystallised from isopropanol, yield 2.5 g, m.p. 93°–95°.

Analysis %: Found: C,61.2; H,4.1; N,7.9; Calculated for C$_9$H$_7$NO$_3$: C,61.0; H,4.0; N,7.9.

(C) 2-Bromomethyl-5-nitrobenzofuran

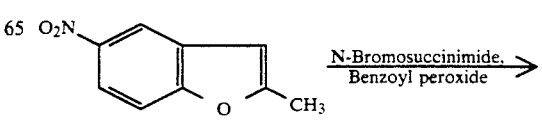

-continued

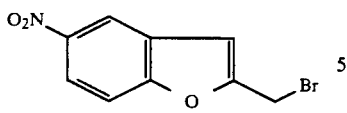

N-Bromosuccinimide (1.1 g, 6.2 mmole) was added portionwise to a solution of 2-methyl-5-nitrobenzofuran (1.0 g, 5.6 mmole) and benzoyl peroxide (50 mg) in carbon tetrachloride (50 ml) and the reaction mixture was heated at reflux temperature for 6 hours in the presence of bright light. The reaction mixture was then cooled, filtered and the filtrate evaporated to dryness. The residue was recrystallised from petroleum ether to give the title compound yield 0.75 g, m.p. 96°-98°.

Analysis %: Found: C,41.7; H,2.4; N,5.3; Calculated for $C_9H_6BrNO_3$: C,42.2; H,2.4; N,5.5.

(D)
N-Methyl-N-(5-nitrobenzofur-2-ylmethyl)-4-nitrophenethylamine

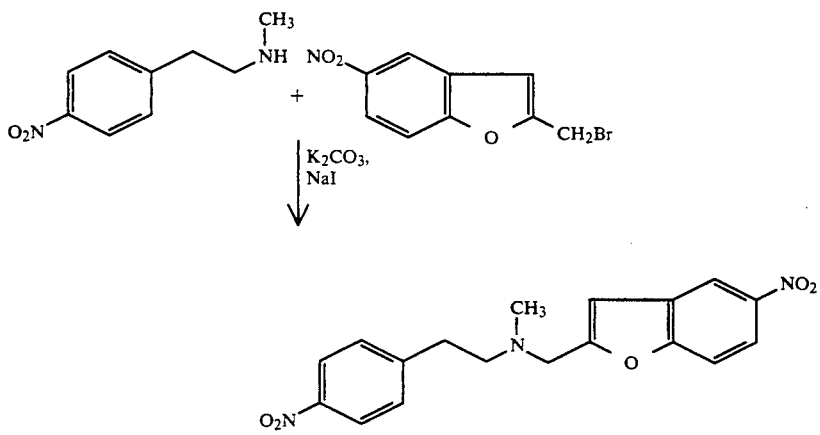

N-Methyl-4-nitrophenethylamine (0.41 g, 2.3 mmole), 2-bromomethyl-5-nitrobenzofuran (0.66 g, 2.6 mmole), sodium iodide (0.39 g, 2.6 mmole) and potassium carbonate (0.36 g, 2.6 mmole) were heated at reflux temperature in acetonitrile (50 ml) for 8 days. The solvent was then evaporated, water was added, and the mixture extracted three times with methylene chloride. The combined organic extracts were washed with water, dried (MgSO4) and evaporated to give a semi-solid which was recrystallised from isopropanol to give the title compound, yield 380 mg.

'H-N.m.r. (DMSO/TFA): δ=8.75 (s, 1H); 8.3 (d, 1H); 8.2 (d, 2H); 7.9 (d, 1H); 7.6 (d, 2H); 7.45 (s, 1H); 4.75 (t, 2H); 3.2 (t, 2H); 2.9 (s, 2H); 2.5 (s, 3H).

PREPARATION 6

(A) 2-Bromomethyl-6-nitrobenzofuran

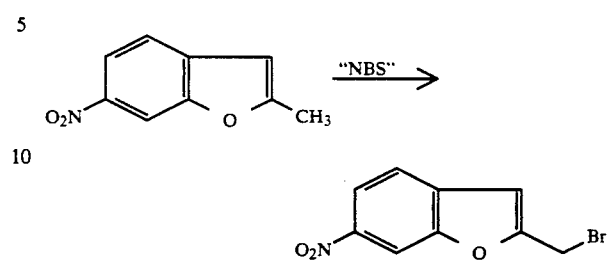

N-Bromosuccinimide ("NBS") (1.11 g, 6.2 mmole) was added to a solution of 2-methyl-6-nitrobenzofuran (1.00 g, 5.65 mmole) and azobisisobutyronitrile (20 mg) in carbon tetrachloride and the mixture was heated at reflux temperature for 1½ hours in the presence of a bright light. The solvent was then evaporated and the residue dissolved in methylene chloride, washed with water, dried (MgSO4), evaporated to dryness and purified by column chromatography on silica eluting with methylene chloride/hexane (7:3). The product-containing fractions were combined and evaporated to give the title compound, yield 1.43 g. 'H-N.m.r. clearly showed that the product contained 20% of 2-dibromomethyl-6-nitrobenzofuran, however, it was not considered necessary to remove this and the product was used directly without further purification.

(B)
N-Methyl-N-(6-nitrobenzoxazol-2-ylmethyl)-4-nitrophenethylamine

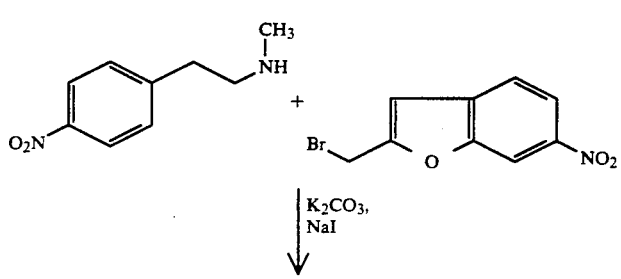

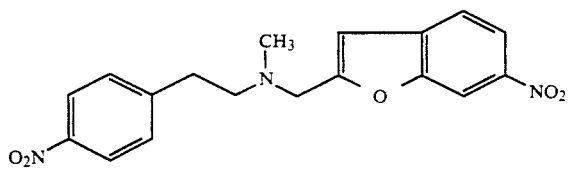

N-Methyl-4-nitrophenethylamine (0.84 g, 4.7 mmole), 2-bromomethyl-6-nitrobenzofuran (1.2 g, 4.7 mmole), sodium iodide (0.7 g, 4.7 mmole) and potassium carbonate (0.71 g, 5.2 mmole) were heated in acetonitrile at the reflux temperature for 18 hours. The cooled reaction mixture was then filtered and the filtrate evaporated to dryness and purified by chromatography on silica eluting with methylene chloride/hexane (1:1) followed by methylene chloride/methanol (19:1). The product-containing fractions were combined and evaporated and the residue was treated with decolourising charcoal in ethanol to afford an oil which solidified on standing. Recrystallisation of the solid from ethanol/methylene chloride gave the title compound, yield 0.27 g, m.p. 69°–69.5°.

Analysis %: Found: C,60.8; H,4.8; N,11.8; Calculated for $C_{18}H_{17}N_3O_5$: C,60.8; H,4.8; N,11.8.

$^1$H-n.m.r. (CDCl$_3$): δ=8.3 (s, 1H); 8.15 (dd, 1H); 8.1 (d, 2H); 7.55 (d, 1H); 7.35 (d, 2H); 6.65 (s, 1H); 3.8 (s, 2H); 2.95 (t, 3H); 2.75 (t, 3H); 2.4 (s, 3H).

PREPARATION 7

(A) 2-Hydroxymethyl-3-methyl-5-nitrobenzofuran

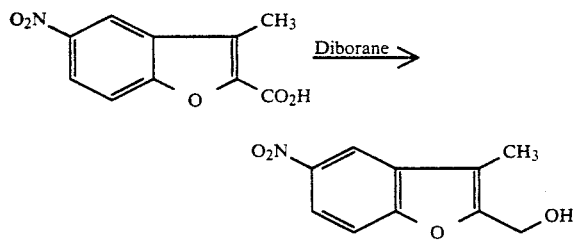

1 Molar diborane in tetrahydrofuran (18.0 ml, 18.0 mmole) was added dropwise to a suspension of 3-methyl-5-nitrobenzofuran-2-carboxylic acid (1.1 g, 5 mmole) in tetrahydrofuran at 0°. Stirring was continued at 0° for 30 minutes then at room temperature for 18 hours when a second portion of diborane (5.0 ml) was added and the reaction mixture was subjected to ultrasound for 2.5 hours. Methanol was then added cautiously to the reaction mixture and the solvent was removed by evaporation. The residue was taken up in ethyl acetate, washed with aqueous sodium bicarbonate, dried (MgSO$_4$), the solvent removed by evaporation in vacuo and purified by column chromatography on silica eluting with methylene chloride. The product-containing fractions were combined and evaporated to give the title compound, yield 0.96 g. A sample was recrystallised from ethyl acetate, m.p. 149°–150°.

Analysis %: Found: C,57.9; H,4.2; N,6.7; Calculated for $C_{10}H_9NO_4$: C,58.0; H,4.4; N,6.8.

(B) 2-Chloromethyl-3-methyl-5-nitrobenzofuran

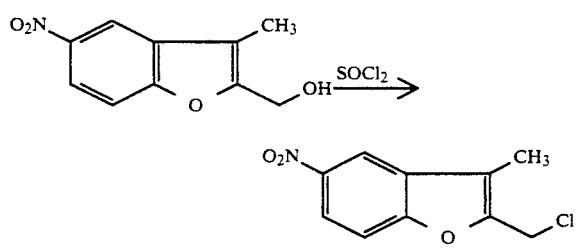

Thionyl chloride (1.48 g, 12.4 mmole) was added dropwise to a solution of 2-hydroxymethyl-3-methyl-5-nitrobenzofuran (0.86 g, 4.15 mmole) in methylene chloride (10 ml) and pyridine (2 drops) and the mixture was stirred at room temperature for 24 hours. The reaction mixture was then diluted with water, the organic phase separated, and the aqueous phase re-extracted with methylene chloride. The combined organic phases were washed with aqueous sodium bicarbonate, dried (Na$_2$SO$_4$) and the solvent evaporated to leave the title compound, 0.93 g. A portion was recrystallised from ethanol, m.p. 141°–142°.

Analysis %: Found: C,52.95; H,3.7; N,6.0; Calculated for $C_{10}H_8ClNO_3$: C,53.2; H,3.6; N,6.2.

PREPARATION 8

N-Methyl-N-(6-nitroquinol-2-ylmethyl)-4-nitrophenethylamine

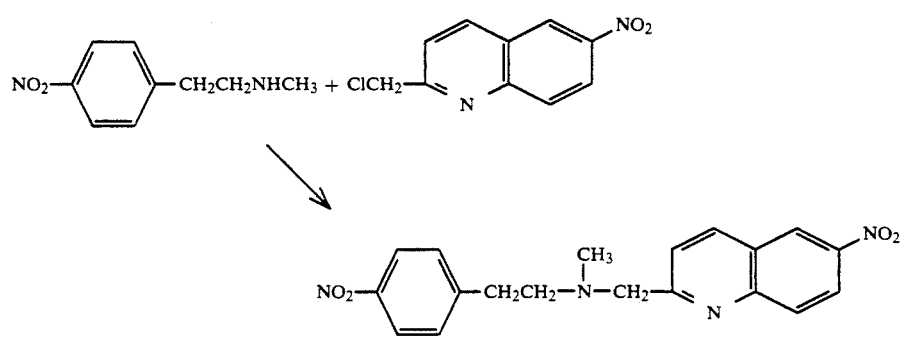

N-Methyl-4-nitrophenethylamine (0.39 g, 2.15 mmole) and 2-chloromethyl-6-nitroquinoline (0.40 g, 2.1 mmole) were heated at reflux temperature in ethanol (30 ml) for 6 hours. The solvent was then evaporated and the residue diluted with 2M hydrochloric acid and extracted with methylene chloride. The aqueous layer was basified with aqueous sodium carbonate (to pH~12) and extracted three times with methylene chloride. These latter organic extracts were combined, dried (MgSO₄) and evaporated giving an oil which was purified by column chromatography on silica eluting with methylene chloride containing methanol (0% up to 1%). The product-containing fractions were combined and evaporated to give a solid which was recrystallised from ethanol to give the title compound, yield 0.21 g, m.p. 104°–105°.

Analysis %: Found: C,62.4; H,4.7; N,15.2; Calculated for $C_{19}H_{18}N_4O_4$: C,62.3; H,4.95; N,15.3.

¹H-n.m.r. (CDCl₃): δ=8.9 (d, 1H); 8.5 (dd, 1H); 8.3–8.1 (m, 3H); 7.6 (d, 1H); 7.35 (d, 1H); 3.95 (s, 2H); 3.0 (t, 2H); 2.8 (t, 2H); 2.4 (s, 3H).

PREPARATION 9

(A) 4-Methanesulphonamidophenethyl mesylate

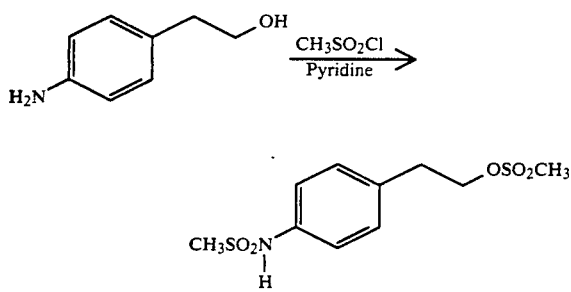

Methanesulphonyl chloride (146.6 g, 1.28 mole) was added dropwise to a solution of 4-aminophenethyl alcohol (82.3 g, 0.6 mole) in pyridine (700 ml) and the mixture was stirred at room temperature for 18 hours. The reaction mixture was then poured into water (700 ml) and the precipitate was collected by filtration, washed with water, dried and recrystallised from ethyl acetate to give the title compound, yield 31 g, m.p. 134°–136°. A further 14.5 g of product was obtained by concentration of the mother liquors in vacuo.

(B) N-Benzyl-N-ethyl-4-methanesulphonamidophenethylamine

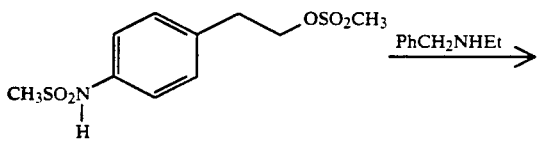

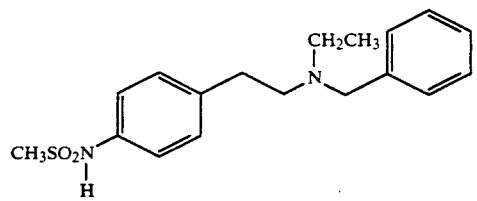

4-Methanesulphonamidophenethyl mesylate (10 g, 34 mmole) and N-ethylbenzylamine (10 ml, 67 mmole) were heated at reflux temperature in ethanol (80 ml) for 3 hours. The solvent was evaporated, the residue taken up in 2M hydrochloric acid and washed twice with methylene chloride. The aqueous layer was basified with sodium bicarbonate (to pH~12) and extracted with methylene chloride. The latter organic extract was dried (MgSO₄) and evaporated to give an oil which solidified when triturated with diisopropyl ether. The solid was filtered off and discarded and the filtrate was evaporated in vacuo to give the title compound as an oil, yield 4.4 g.

¹H-N.m.r. (CDCl₃): δ=7.2 (s, 5H); 7.05 (s, 4H); 3.6 (s, 2H); 2.95 (s, 3H); 2.70 (s, 4H); 2.40 (q, 2H); 1.1 (t, 3H).

(C) N-Ethyl-4-methanesulphonamidophenethylamine

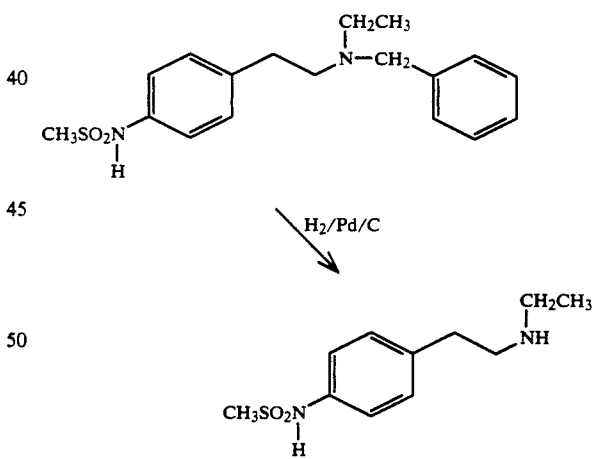

N-Benzyl-N-ethyl-4-methanesulphonamidophenethylamine (4.3 g, 12.9 mmole) was stirred under a hydrogen atmosphere (50 p.s.i.=344.7 kPa) in ethanol (50 ml) containing 10% Pd/C (0.5 g) for 5 hours. The mixture was then filtered, evaporated and the residue triturated with ether to give the title compound, yield 2.6 g, m.p. 125°–128°.

N.m.r. (CDCl₃/DMSO): δ=7.06 (s, 4H); 4.9 (s, 2H); 2.36 (s, 2H); 2.8 (s, 2H); 2.65 (q, 2H); 1.05 (t, 3H).

PREPARATION 10

(A)
N-Methyl-N-(3-methyl-5-nitrobenzofur-2-ylmethyl)-4-methanesulphonamidophenethylamine

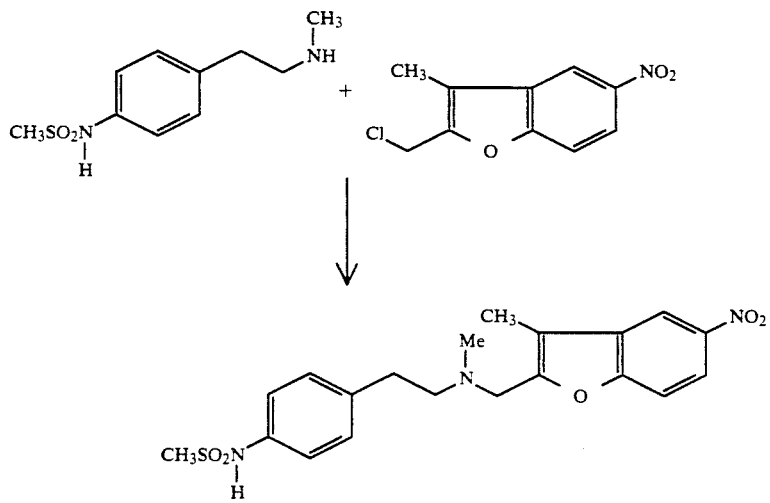

N-Methyl-4-methanesulphonamidophenethylamine (1.66 g, 7.3 mmole) and 2-chloromethyl-3-methyl-5-nitrobenzofuran (see Preparation 7B—0.82 g, 3.6 mmole) were heated at reflux temperature in ethanol (20 ml) for 3 hours. The solvent was then evaporated and the residue was purified by column chromatography on silica eluting with methylene chloride/hexane (4:1) followed by methylene chloride containing methanol (0% up to 5%). The product-containing fractions were combined and evaporated, and the residue was recrystallised from ethanol to give the title compound, yield 1.52 g, m.p. 124°-124.5°.

Analysis %: Found: C,57.7; H,5.65; N,10.0; Calculated for $C_{20}H_{23}N_3O_5S$: C,57.5; H,5.55; N,10.1.

$^1$H-n.m.r. (CDCl$_3$): δ=8.45 (d, 1H); 8.25 (dd, 1H); 7.5 (d, 1H); 7.2 (q, 4H); 3.8 (s, 2H); 3.05 (s, 3H); 2.9 (t, 2H); 2.75 (t, 2H); 2.4 (s, 3H); 2.35 (s, 3H).

(B)
N-Methyl-N-(3-methyl-5-aminobenzofur-2-ylmethyl)-4-methanesulphonamidophenethylamine

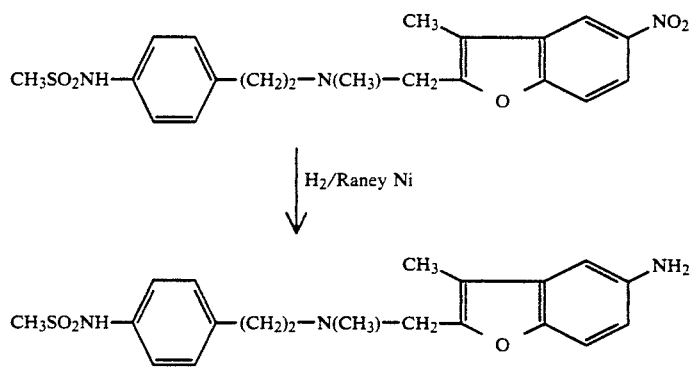

Catalytic hydrogenation of the product of part (A) (0.7 g) similarly to Preparation 1(C) with a reaction time of 4 hours gave the title compound (0.65 g).

$^1$H-N.m.r. (CD$_3$OD): δ=7.25 (m, 6H); 6.9 (d, 1H); 6.8 (dd, 1H); 3.8 (s, 2H); 2.95 (s, 3H); 2.9 (m, 2H); 2.7 (m, 2H); 2.4 (s, 3H); 2.35 (s, 3H).

PREPARATION 11

(A) N-Ethyl-N-(6-nitroquinol-2-ylmethyl)-4-methanesulphonamidophenethylamine

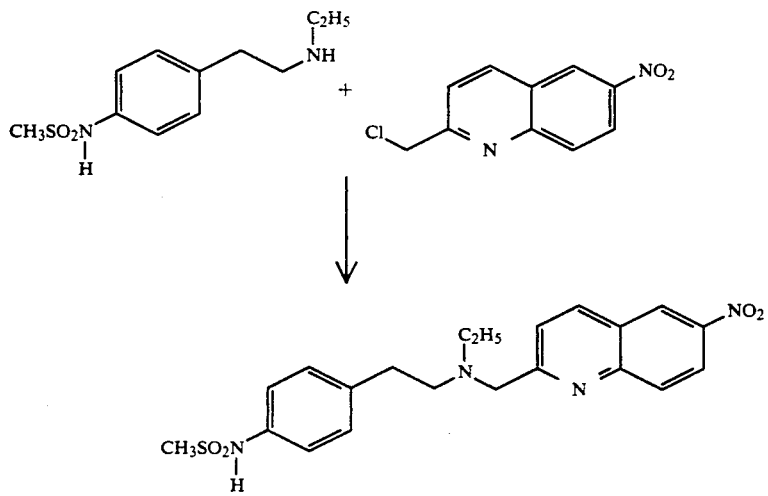

N-Ethyl-4-methanesulphonamidophenethylamine (see Preparation 9(C)—1.7 g, 7.0 mmole) and 2-chloromethyl-6-nitroquinoline (0.78 g, 4.1 mmole) were heated at reflux temperature in ethanol (50 ml) for 4 hours. The solvent was then evaporated and the residue was diluted with aqueous sodium bicarbonate and extracted with methylene chloride. The organic layer was dried (MgSO$_4$), evaporated and the residue was purified by column chromatography on silica eluting with methylene chloride. The product-containing fractions were combined and evaporated to give the title compound as an oil, yield 0.56 g.

'H-N.m.r. (CDCl$_3$): δ=8.6 (d, 1H); 8.3-8.0 (m, 2H); 7.6 (d, 1H); 7.1 (s, 1H); 7.0 (s, 4H); 3.9 (s, 2H); 2.9 (s, 2H); 2.7 (s, 2H); 2.65 (q, 2H); 1.05 (t, 3H).

(B) N-Ethyl-N-(6-aminoquinol-2-ylmethyl)-4-methanesulphonamidophenethylamine

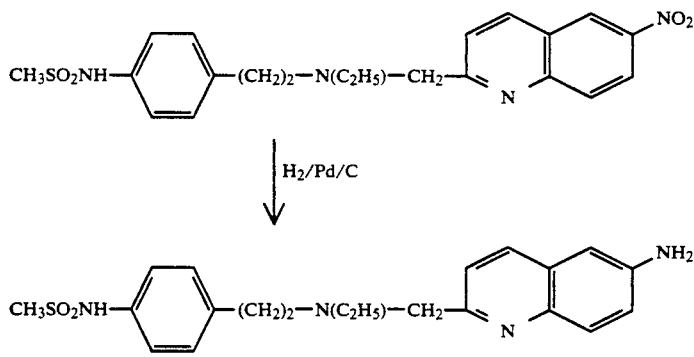

The product of part (A) (0.55 g) was catalytically hydrogenated similarly to Preparation 1(C) but using H$_2$ over 5% Pd on C in ethyl acetate at 15 p.s.i. (103.4 kPa) for 3 hours, giving the title compound (0.51 g).

'H-N.m.r. (cDCl$_3$): δ=7.7 (d, 1H); 7.5 (d, 1H); 7.15 (d, 1H); 6.9 (broad s, 5H); 6.65 (d, 1H); 3.75 (s, 2H); 2.95 (s, 3H); 2.6 (s, 4H); 2.5 (q, 2H); 0.95 (t, 3H).

PREPARATION 12

(A) 6-Amino-2-methylquinoline

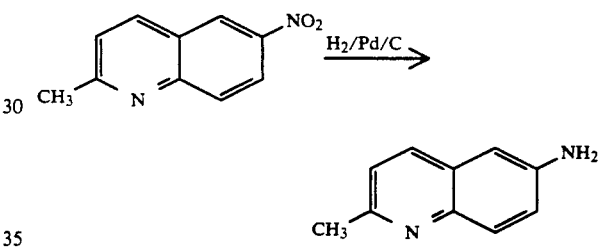

2-Methyl-6-nitroquinoline (18.8 g) was stirred under a hydrogen atmosphere at 30 p.s.i. (equivalent to 206.8 kPa) for 2 hours in ethanol solution containing 5% Pd/C. The catalyst was then removed by filtration, the filtrate evaporated to small volume in vacuo, and the resultant precipitate collected by filtration, washed with ethanol and ether, and dried to give the title compound, yield 13.2 g, m.p. 188°-189°.

Analysis %: Found: C,75.7; H,6.4; N,17.6; Calculated for C$_{10}$H$_{10}$N$_2$: C,75.9; H,6.4; N,17.7.

(B) 6-Methanesulphonamido-2-methylquinoline

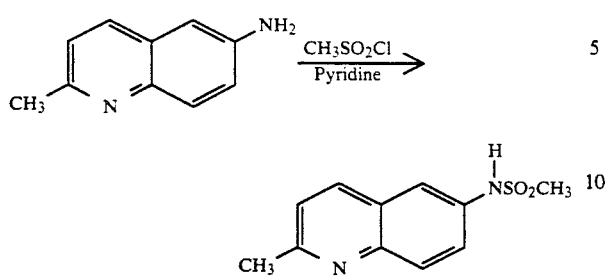

Methanesulphonyl chloride (6.2 ml) was added dropwise to a stirred solution of 6-amino-2-methylquinoline (12.5 g) in pyridine (100 ml) cooled to 5°. Stirring was continued for 17 hours at room temperature. The pyridine was then removed by evaporation in vacuo, the residue diluted with aqueous sodium bicarbonate, and extracted three times with methylene chloride. The combined organic extracts were combined, dried (MgSO$_4$) and evaporated in vacuo to give the title compound, yield 13.0 g, m.p. 151°–153°.

Analysis %: Found: C,55.4; H,5.2; N,11.6; Calculated for C$_{11}$H$_{12}$N$_2$O$_2$S: C,55.9; H,5.1; N,11.9.

(C) 6-Methanesulphonamido-2-methylquinoline-1-oxide

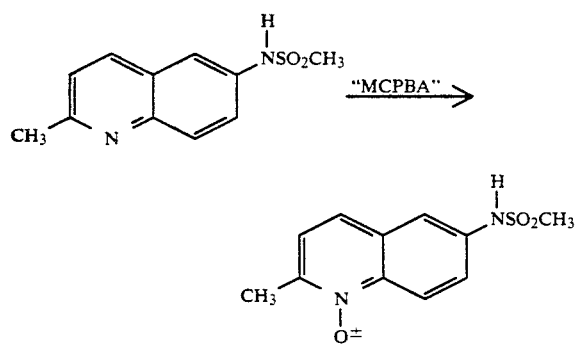

m-Chloroperbenzoic acid ("MCPBA") (5.2 g) was added portionwise to a solution of 6-methanesulphonamido-2-methylquinoline (6 g) in methylene chloride and stirring was continued for 17 hours. The reaction mixture was then diluted with aqueous sodium bicarbonate and the organic layer was separated. The aqueous layer was extracted with methylene chloride. The combined organic layers were washed with aqueous sodium bicarbonate, dried (MgSO$_4$) and evaporated in vacuo to give a solid which was recrystallised from ethanol to give the title compound, yield 1.6 g, m.p. 241°–243°.

Analysis %: Found: C,52.5; H,4.95; N,11.0; Calculated for C$_{11}$H$_{12}$N$_2$O$_3$S: C,52.4; H,4.8; N,11.1.

(D) 2-Chloromethyl-6-methanesulphonamidoquinoline

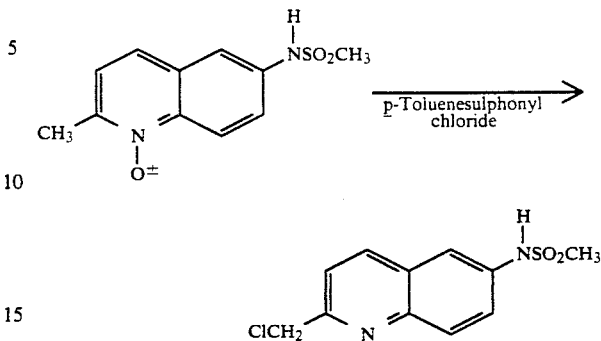

6-Methanesulphonamido-2-methylquinoline-1-oxide (1.65 g) and p-toluenesulphonyl chloride (1.72 g) were heated under reflux for 1 hour in 1,2-dichloroethane solution, and the reaction mixture was then stood at room temperature for 17 hours. The reaction mixture was then washed twice with aqueous sodium bicarbonate, dried (MgSO$_4$) and evaporated in vacuo. The residue was purified by column chromatography on silica eluting with methylene chloride containing methanol (0% up to 1%). The product-containing fractions were combined and evaporated to give a gum which solidified when triturated with ether. Recrystallisation from toluene gave the title compound, yield 0.75 g, m.p. 160°–162°.

Analysis %: Found: C,49.3; H,3.9; N,10.1; Calculated for C$_{11}$H$_{11}$N$_2$O$_2$ClS: C,48.8; H,4.1; N,10.35.

PREPARATION 13

(A) 2-Chloromethyl-5-nitrobenzo[b]thiophene

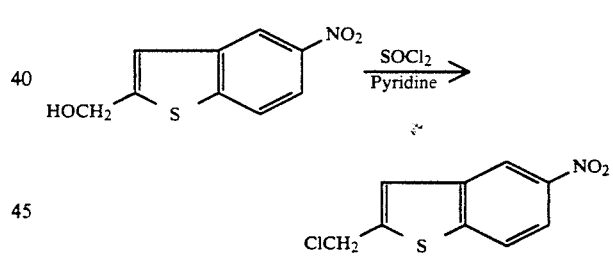

Thionyl chloride (1.0 ml) was added dropwise to a stirred mixture of 5-nitrobenzo[b]thiophene-2-methanol (1.0 g) and pyridine (2 drops) in dichloromethane (10 ml). The solution was stirred at room temperature for 4 hours and then washed with water followed by aqueous sodium bicarbonate solution, and then dried (Na$_2$SO$_4$). The solvent was evaporated and the residue was chromatographed on silica gel. Elution with dichloromethane gave a solid which was crystallised from ethyl acetate to give the title compound (0.73 g), m.p. 110°–112°, used directly in the next stage.

(B) N-Methyl-N-[5-nitro-2-benzo[b]thienylmethyl]-4-nitrophenethylamine

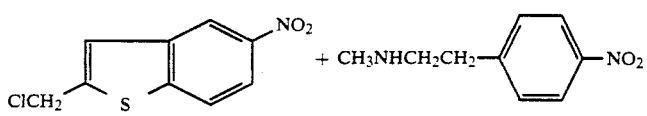

-continued

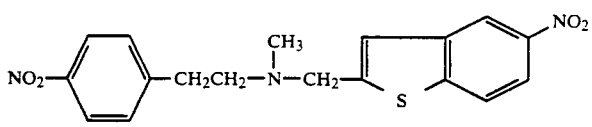

A mixture of the product of part (A) above (3.20 g), N-methyl-4-nitrophenethylamine (2.52 g), anhydrous potassium carbonate (4.0 g) and acetonitrile (40 ml) was heated under reflux with stirring for 20 hours and then cooled and filtered. The residue was washed with acetonitrile, and the combined filtrate and washings were evaporated to give an oil which was chromatographed on silica gel. Elution with dichloromethane first gave impurity followed by pure product. The product-containing fractions were evaporated to give the title compound (4.17 g), m.p. 76°–78° (from isopropanol).

Analysis %: Found: C,57.8; H,4.4; N,11.1; $C_{18}H_{17}N_3O_4S$ requires: C,58.2; H,4.6; N,11.3.

(C)
N-Methyl-N-[5-amino-2-benzo[b]thienylmethyl]-4-aminophenethylamine

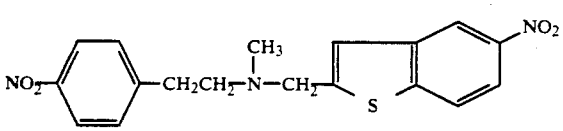

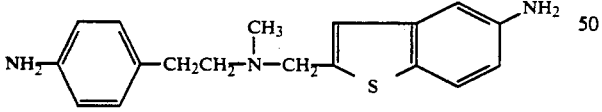

A mixture of the product of (B) above (1.0 g) and stannous chloride dihydrate (6.07 g) in ethanol (100 ml) was heated under reflux for 8 hours and then evaporated. An excess of 20% aqueous sodium hydroxide solution was added and the mixture was extracted several times with dichloromethane. The combined organic extracts were washed with water, dried ($Na_2SO_4$) and evaporated to give an oil which was chromatographed on silica gel. Elution with dichloromethane/methanol (99:1) gave impurity and then further elution with dichloromethane/methanol (98:2) gave, after collection and evaporation of appropriate fractions, the product as an oil (0.30 g) which was used immediately in the procedure of Example 6.

PREPARATION 14

(A)
4-[2-(Methanesulphonyloxy)ethyl]-methanesulphonanilide

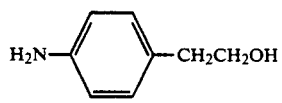

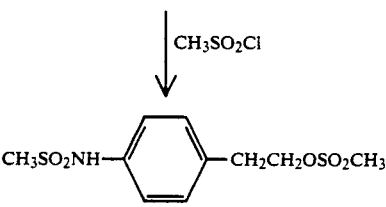

Methanesulphonyl chloride (50 ml) was added dropwise over 0.5 hours to a stirred solution of 4-aminophenethyl alcohol (41.15 g) in pyridine (350 ml) at 0°. The mixture was allowed to warm to room temperature and stirred overnight. The mixture was then poured onto water (700 ml) from which an orange solid crystallised. After filtration, the solid was dissolved in methylene chloride, dried over magnesium sulphate, filtered and the filtrate re-evaporated. Crystallisation of the resultant solid from ethyl acetate gave the title compound, 45.5 g, m.p. 136°–137°.

Analysis %: Found: C,40.6; H,5.2; N,4.9; Calculated for $C_{10}H_{15}NO_5S_2$: C,40.9; H,5.15; N,4.8.

(B) 4-[2-(Methylamino)ethyl]methanesulphonanilide

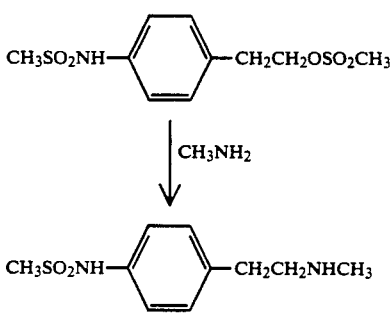

To a solution of 4-[2-(methanesulphonyloxy)ethyl]-methanesulphonanilide (10.3 g) in ethanol (20 ml) was added a solution of methylamine in industrial methylated spirits (30 ml of 33% solution). The mixture was heated with stirring at 85° in a pressure vessel for 17 hours. After cooling, the resultant solution was evaporated to dryness, the residue dissolved in water, and the resultant solution basified by the addition of sodium hydroxide (1.4 g) in water (12 ml). Evaporation gave an off-white solid which was chromatographed on silica ("Kieselgel 60"-Trade Mark) eluting with methylene chloride/methanol (3:1). Collection and evaporation of suitable fractions gave an off-white solid (4.8 g) which crystallised from ethyl acetate/methanol to give the title compound, 1.8 g, m.p. 133°–135°.

Analysis %: Found: C,52.5; H,7.1; N,12.2; Calculated for $C_{10}H_{16}N_2O_2S$: C,52.6; H,7.1; N,12.3.

We claim:

1. An organic compound of the formula:

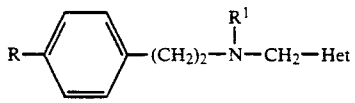

or a pharmaceutically acceptable salt thereof, wherein
R is $—NHSO_2(C_1-C_4)$ alkyl;
$R^1$ is $C_1-C_4$ alkyl; and
"Het" is a benzo-fused heterocyclic group of the formula:

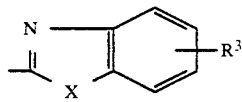

wherein $R^3$ is $—NHSO_2(C_1-C_4$ alkyl), and X is oxygen or sulfur.

2. A compound as claimed in claim 1 wherein "Het" is 5-methanesulphonamidobenzoxazol-2-yl.

3. A compound as claimed in claim 1 wherein each of R and $R^3$ is $—NHSO_2CH_3$, $R^1$ is methyl or ethyl, and X is oxygen or sulfur.

4. A compound as claimed in claim 3 wherein $R^1$ is methyl, $R^2$ is hydrogen and X is oxygen.

5. A compound as claimed in claim 3 wherein "Het" is a benzo-fused heterocyclic group of the formula:

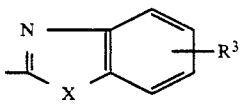

wherein $R^3$ is attached to either the a- or b- position of "Het".

6. N-Methyl-N-(5-methanesulphonamidobenzoxazol-2-ylmethyl)-4-methanesulphonamidophenethylamine.

7. A pharmaceutical composition comprising a pharmaceutically acceptable carrier or diluent and an effective anti-arrhythmic amount of a compound as claimed in claim 1.

8. A method for preventing or reducing cardiac arrhythmias in the treatment of a mammalian subject afflicted with an impaired cardiac pump function, which comprises administering to said subject an effective anti-arrhythmic amount of a compound which is a class III anti-arrhythmic agent of the structural formula as claimed in claim 1.

* * * * *